(12) United States Patent
Garton et al.

(10) Patent No.: US 7,422,904 B2
(45) Date of Patent: Sep. 9, 2008

(54) METHOD OF OPERATING A FIXED BED REACTOR UNDER PREDETERMINED HYDRAULIC CONDITIONS

(75) Inventors: Ronald D. Garton, Baton Rouge, LA (US); David G. Woods, Beaumont, TX (US); Hans G. Korsten, Fairfax, VA (US); Pierre J. Osterrieth, Baton Rouge, LA (US); Brian C. McClaine, Baton Rouge, LA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 373 days.

(21) Appl. No.: 11/051,185

(22) Filed: Feb. 4, 2005

(65) Prior Publication Data

US 2006/0178540 A1    Aug. 10, 2006

(51) Int. Cl.
*G01N 31/10* (2006.01)
*G05B 13/00* (2006.01)
*B01J 8/02* (2006.01)

(52) U.S. Cl. .................. 436/34; 422/62; 422/110; 422/111; 422/129; 436/37; 436/55; 436/127; 436/131; 436/139; 436/159; 436/181; 700/266

(58) Field of Classification Search .................. 422/62, 422/110–111, 129–130, 211, 216, 219; 436/34, 436/37, 55, 127, 131, 139–142, 155, 159, 436/181; 700/266; 702/22, 24, 30
See application file for complete search history.

(56) References Cited

U.S. PATENT DOCUMENTS

| | | | |
|---|---|---|---|
| 4,288,640 A | 9/1981 | Schuster et al. | 568/855 |
| 4,960,960 A | 10/1990 | Harrison et al. | 568/881 |
| 5,081,321 A | 1/1992 | Fukuhara et al. | 568/881 |
| 5,093,535 A | 3/1992 | Harrison et al. | 568/881 |
| 6,262,317 B1 | 7/2001 | Becker et al. | 568/861 |
| 6,492,564 B1 | 12/2002 | Wiese et al. | 568/451 |
| 6,680,414 B2 | 1/2004 | Knoop et al. | 568/830 |
| 6,774,275 B2 | 8/2004 | Smith, Jr. et al. | 585/731 |

FOREIGN PATENT DOCUMENTS

| | | |
|---|---|---|
| FR | 2 597 113 | 4/1987 |
| GB | 1 362 071 | 7/1974 |
| WO | WO 03/042333 | 5/2003 |

OTHER PUBLICATIONS

Christofides, P. D. et al, Computers & Chemical Engineering 1996, 20 (Suppl. B), S1071-S1076.*
Lamine, A. S. et al, Chemical Engineering Science 1996, 51, 3813-3827.*
Toppinen, S. et al, Chemical Engineering Science 1996, 51, 4335-4345.*
Motil, B. J. et al, AIChE Journal 2003, 49, 557-565.*

(Continued)

*Primary Examiner*—Arlen Soderquist
(74) *Attorney, Agent, or Firm*—Andrew B. Griffis

(57) ABSTRACT

The invention provides a system for designing, operating, monitoring and/or diagnosing a chemical reaction, particularly a hydrotreating process, using a fixed bed catalytic reactor.

9 Claims, 7 Drawing Sheets

OTHER PUBLICATIONS

Huang, X. et al, Chemical Engineering Science 2003, 58, 3465-3471.*

Marwan, H. et al, Chemical Engineering & Technology 2003, 26, 996-1002.*

Bartelmus, G. et al, Chemical Engineering and Processing 2003, 43, 169-179.*

Datsevich, L. B. et al, Applied Catalysis, A: General 2004, 261, 143-161.*

Lange, R. et al, Chemical Engineering Science 2004, 59, 5355-5361.*

Cheng et al., "Influence of Hydrodynamic Parameters on Performance of a Multiphase fixed-bed reactor under phase transition" *Chemical Engineering Science*, vol. 57 pp. 3407-3413, (2002).

Burghardt et al., "Hydrodynamics of a three-phase fixed-bed reactor operating in the pulsing flow regime at an elevated pressure," *Chemical Engineering Science*, vol. 57, pp. 4855-4863, (2002).

Attou et al., "A two-fluid hydrodynamic model for the transition between trickle and pulse flow in a cocurrent gas-liquid packed-bed reactor," *Chemical Engineering Science*, vol. 55, pp. 491-511, (2000).

Morsi et al., "Flow patterns and Some Holdup Experimental Data in Trickle-Bed Reactors for Foaming, Nonfoaming, and Viscous Organic Liquids," *AIChE Journal*, vol. 24, No. 2, pp. 357-360, (1978).

Sherman et al., "Symposium: Modeling and Troubleshooting of Commercial-Scale Reaction Systems," *American Institute of Chemical Engineers*, 71$^{st}$ Annual Meeting, Miami Beach, Florida, Nov. 12-16, 1978.

Stuber et al., "Partial Hydrogenation in an Upflow Fixed-Bed Reactor: A Multistage Operation for Experimental Optimization of Selectivity," *Ind. Eng. Chem. Res.*, vol. 42, pp. 6-13, (2003).

Gupta et al., "Cocurrent Gas-Liquid Downflow in Packed Beds," *Handbook of Fluids in Motion, AnnArbor Science*, pp. 515-537, (1983).

Guray Tosun, "A Study of Cocurrent Downflow of Nonfoaming Gas-Liquid Systems in a Packed Bed. 1. Flow Regimes: Search for a Generalized Flow Map," *Ind. Eng. Chem. Process Des. Dev.*, vol. 23, pp. 29-35 (1984).

Holub et al., "Pressure Drop, Liquid Holdup, and Flow Regime Transition in Trickle Flow," *AIChE Journal*, vol. 39, No. 2, pp. 302-321, (1993).

H. P. Hofmann, "Multiphase Catalytic Packed-Bed Reactors," *Catal. Rev.-Sci. Eng.*, vol. 17, No. 1, pp. 71-117, (1978).

Borkink et al., "Influence of Tube and Particle Diameter on Heat Transport in Packed Beds," AIChE Journal, vol. 38, No. 5, pp. 703-715, (1992).

Sai et al., "Pressure Drop in Gas-Liquid Downflow Through Packed Beds," AIChE Journal, vol. 33, No. 12, pp. 2027-2036, (1987).

Al-Dahhan et al., "High-Pressure Trickle-Bed Reactors: A Review," Ind. Eng. Chem. Res., vol. 36, No. 18 pp. 3292-3314, (1997).

Moreira et al., Influence of Gas and Liquid Flow Rates and the Size and Shape of Particles on the Regime Flow Maps Obtained in Concurrent Gas-Liquid Downflow and Upflow through Packed Beds, *Ind. Eng. Chem. Res.* vol. 42, pp. 929-936, (2003).

Carbonell et al, "Effectiveness Factors and Mass Transfer in Trickle-Bed Reactors," *AIChE Journal*, vol. 25, No. 2, pp. 272-283, (1979).

Gianetto et al., "Hydrodynamics and Solid-Liquid Contacting Effectivenss in Trickle-Bed Reactors," *AIChE Jounal*, vol. 24, No. 6, pp. 1087-1104, (1978).

Worstell et al., "Propyerly Size Fixed-Bed Catalytic Reactors," *Chemical Engineering Progress*, pp. 31-37, (1993).

Morlta et al., "Mass Transfer and Contacting Efficiency in a Trickle-Bed Reactor," *Ind. Eng. Chem. Fundam.* vol. 17, No. 2, pp. 113-120, (1978).

M. P. Dudukovic, "Catalyst Effectiveness Factor and Contacting Efficiency in Trickle-Bed Reactors," *AIChE Journal*, vol. 23, No. 6, pp. 940-944, (1977).

Borio et al., "Cocurrently-Cooled Fixed-Bed Reactors: A Simple Approach to Optimal Cooling Design," *AIChE Journal*, vol. 35, No. 11, pp. 1899-1989, (1989).

Satterfield et al., "Mass Transfer Limitations in a Trickle-Bed Reactor," *AIChE Journal*, pp. 226-234, (1969).

Charpentier et al., "Some Liquid Holdup Experimental Data in Trickle-Bed Reactors for Foaming and Nonfoaming Hydrocarbons," AIChE Journal, vol. 21, No. 6, pp. 1213-1218, (1975).

E. Talmor, "Two-Phase Downflow Through Catalyst Beds," AIChE Journal, Vo.23, No. 6, pp. 868-873, (1977).

E. Talmor, "Two-Phase Downflow Through Catalyst Beds," AIChE Journal, Vo.23, No. 6, pp. 874-878, (1977).

Ng et al., "Trickle-Bed Reactors," Chemical Engineering Progress, pp. 55-70, (1987).

Motil et al., "Effects of Gravity on Cocurrent Two-Phase Gas-Liquid Flows Through Packed Columns," Prepared for the 39$^{th}$ Aerospace Sciences Meeting and Exhibit, Reno, Nevada, Jan. 8-11, 2001, NASA/TM-2001-210705, p. 1-10, (2001).

* cited by examiner

METHOD OF OPERATING A FIXED BED REACTOR UNDER PREDETERMINED HYDRAULIC CONDITIONS

FIELD OF THE INVENTION

The invention relates to the design, operation, and/or diagnosis of a fixed bed reactor and to the use of said reactor in a process. In an embodiment, the invention is directed to a process for the hydrogenation of aldehydes and ketones to make alcohols, and the design, operation and/or diagnosis of fixed-bed, gas-liquid, downflow catalytic reactor used for said process.

BACKGROUND OF THE INVENTION

The fixed bed catalytic reactor is a well-known, elegant device for carrying out a chemical reaction utilizing a catalyst. There are myriad advantages associated with this type of reactor, such as: the apparatus is typically simple to design, there are no moving parts to wear out, the catalyst stays in the reactor, it is easy to separate the reaction mixture from the catalyst, heat can be added or removed by, for example, the addition of cold gas or liquid quench, internal or external heat exchanger(s), wall heat transfer (e.g., in the case of small diameter tubes like bench scale units or multi-tube-bundle reactors), or the reactor can be operated adiabatically.

There are numerous configurations of fixed bed catalytic reactors, the most common of which is probably cocurrent gas-liquid downflow, described, for instance, by R. Gupta, in "Cocurrent Gas-Liquid Downflow in Packed Beds", Chapter 19, of the *Handbook of Fluids in Motion* (1983). Other configurations include cocurrent upflow and countercurrent operations.

Whatever the specific configuration, theoretically the fixed bed catalytic reactor is expected to provide, among other attributes, sufficient volume and residence time to provide the desired conversion, provide sufficient mass transfer rate of reactants and products through the gas-liquid interface and through the liquid film on the surface of catalyst particles, provide effective use of the entire catalyst particle and active sites throughout the cross section of particles in the bed, provide uniform flow distribution over entire width and length of bed to utilize all of the catalyst, provide conditions where gas and liquid phases remain homogeneously mixed and do not separate, allow for conditions where all the catalyst is adequately wetted such that both reactants are present and heat is transferred effectively from all zones in the reactor, provide an effective method for controlling temperature in a safe operating window or effective range to maximize reaction selectivity, product quality, catalyst life, and the like. See for instance H. Hofmann: "Multiphase Catalytic Packed Bed Reactors", Catal. Rev. Sci. Eng. 17 (1978) 71-117. However, it is still a long-sought goal to achieve all of the aforementioned attributes in a commercial reactor.

An example of the type of process that can be carried out in such a reactor is hydrogenation. Heterogeneous catalytic hydrogenation processes of various kinds are widely practiced on a commercial scale and are used for hydrogenation of a wide variety of organic feedstocks.

Specific examples include hydrogenation of aldehydes and ketones to alcohols, of unsaturated hydrocarbons to saturated hydrocarbons, of acetylene-derived chemicals to saturated materials, of unsaturated fatty acids to saturated fatty acids, of esters of unsaturated fatty acids to esters of partially or fully hydrogenated fatty acids, of nitrites to primary amines, of certain sugars to polyhydroxyalcohols. Other examples include the hydrogenation of quinones (for example the hydrogenation of 2-ethylanthraquinone as a step in the production of hydrogen peroxide), the production of cyclohexanol from cyclohexanone, the production of iso-propanol from acetone, and the hydrogenation of unsaturated hydrocarbons such as in the production of cyclohexane from benzene.

Typical catalysts for such hydrogenation reactions include Group VIII metal catalysts such as cobalt, nickel, rhodium, palladium and platinum (using the traditional CAS version of the Periodic Table; see Chemical and Engineering News, 63(5) 27, 1985), and also other metals such as copper, zinc, and molybdenum.

Production of butane-1,4-diol by hydrogenation of but-2-yn-1,4-diol is an example of hydrogenation of an acetylene-derived chemical; a suitable catalyst for this reaction has been described as a granular nickel-copper-manganese on silica gel. The production of stearic acid by catalytic hydrogenation of the corresponding unsaturated acids, linoleic acid and linolenic acid, using a nickel, cobalt, platinum, palladium, chromium or copper/zinc catalyst, is an example of the hydrogenation of unsaturated fatty acids to yield saturated fatty acids. So-called "hardening" of vegetable oils is an example of hydrogenation of esters of unsaturated fatty acids. Production of beta-phenylethylamine by hydrogenation of benzyl cyanide is an example of hydrogenation of a nitrile. As examples of hydrogenation of sugars to polyhydroxyalcohols there can be mentioned hydrogenation of ketose and aldose sugars to hexahydroxyalcohols, for example hydrogenation of D-glucose to sorbitol and of D-mannose to mannitol.

An important route to $C_3$ and higher alcohols involves hydroformylation of olefins, such as ethylene, propylene, and butene-1, to yield the corresponding aldehyde having one more carbon atom than the starting olefin, followed by hydrogenation to the alcohol. The commercially important Oxo Process comprises such a hydroformylation process, followed by hydrogenation. Thus, hydroformylation of ethylene yields propionaldehyde and propylene yields a mixture of n- and iso-butyraldehyde, followed by catalytic hydrogenation to the corresponding alcohols, e.g. n-propanol and n-butanol. The important plasticiser alcohol 2-ethylhexanol may be made, for instance, by alkali-catalyzed condensation of n-butyraldehyde to yield the unsaturated aldehyde, 2-ethyl-hex-2-enal, which is then hydrogenated to yield the desired 2-ethylhexanol. Historically the preferred catalysts for such aldehyde hydrogenation reactions are the Group VIII metal catalysts, particularly nickel, palladium, platinum, or rhodium. Numerous other systems have been proposed. The Oxo Process and variations thereon are the subject of numerous patents and patent applications, more recent examples of which are WO2003083788A2 and WO2003082789A2, and which in turn recite numerous references to the same subject matter.

Hydrodesulphurisation is another commercially important hydrogenation reaction. This is the removal of complex organic sulfur compounds, such as sulfides, disulfides, benzothiophene and the like, from a mixed hydrocarbon feedstock by catalytic reaction with hydrogen to form hydrogen sulfide.

Similar, and often simultaneously to hydrodesulfurization is hydrodenitrogenation, where complex organic nitrogen components are converted with hydrogen to form hydrocarbons and ammonia. Typical organic nitrogen components are pyrrole, pyridine, amines and benzonitriles.

Another refining application is hydrocracking which is used to reduce the boiling point of the feed by cracking large molecules into smaller ones and adding hydrogen to them using a bifunctional catalyst.

Catalytic hydrotreating is, in all the above cases, a heterogeneous process, typically operated as a vapour phase process or as a liquid/gas phase process. In the conventional multi-stage hydrogenation processes the hydrogen-containing gas and the material to be hydrogenated are fed through the plant in co-current or in counter-current fashion. In order to achieve good economy of hydrogen usage, sometimes a recycle gas is used, typically comprising $H_2$ and a diluent such as methane other light product gases of the main process.

The term "trickle bed reactor" or "trickle bed state" is often used to describe a reactor in which a liquid phase and a gas phase flow cocurrently downward through a fixed bed of catalyst particles while reaction takes place. However, these reactors can be operated in various flow regimes, depending on vapor and liquid flow rates and properties. At sufficiently low liquid and gas flow rates the liquid trickles over the packing in essentially a laminar film or in rivulets, and the gas flows continuously through the voids in the bed. This is termed the gas continuous region or more specific "trickle flow regime" and is the type encountered usually in refinery applications, in which typically large excess of hydrogen is required to prevent coking and to keep the concentration of catalyst poison such as hydrogen sulfide that is formed during the reaction low. It should be noted, however, that the operating window of trickle flow is very wide and not only determined by flow rates (see, e.g., E. Talmor, AIChE Journal, Vol. 23, No. 6, 868-874 (November 1977) discussed more fully below). Thus, for instance, and without wishing to be bound by theory, it may be possible to operate with low liquid rates but at relatively high gas rates, too.

As gas and/or liquid flow rates are increased there is encountered behavior described as rippling, slugging, known in the art as "pulse flow regime". Such behavior may be characteristic of the higher operating rates often encountered in commercial petroleum processing. Pulsing is caused by alternating zones that are rich in vapor or in liquid. It is often called "high interaction flow regime". At high liquid rates and sufficiently low gas rates, the liquid phase becomes continuous and the gas passes in the form of bubbles; this is termed "dispersed bubble flow" or "bubble flow regime" and is characteristic of some chemical processing in which liquid flow rates (per unit cross section area of the reactor) may be comparable to but more typically are much higher than the highest encountered in petroleum processing, but where gas/liquid ratios are much less.

Fixed bed hydrogenation reactors running in the bubble flow regime, i.e., relatively low volumetric gas to liquid ratio can have a tendency for the phases to separate. Without wishing to be bound by theory, such phase separation may happen because the separate flows have a pressure drop over the reactor or part of the reactor that is lower than the mixed phase pressure drop would be; notionally, this may result in loss of much of the reaction due to starvation of one component in those vapor-liquid separated zones, "hot-spots" resulting from the localized accumulation of reaction heat that is not transported away by an adequate flow of liquid, and/or overall axial or centerline temperature profile showing a higher $\Delta T$ than what is theoretically possible under ideal flow conditions.

The aforementioned problem is avoided in most refinery processes where a large excess of gas is recycled over the reactor, putting it into the trickle flow or pulsing regime. Another way to solve the problem is to use high liquid velocities, with resulting high pressure drop along with high energy consumption. Both alternatives are high cost solutions.

What is needed is a simple and direct way of optimizing reactor operation and/or design to combine the key variables such as pressure, feed flows, particle size, bed void fraction, and reactor dimensions, and to do so economically. Unfortunately, the literature appears to be consistent in describing the phenomena of multiphase flow in a packed bed as complex and not well understood. Once the process chemistry, catalyst, and temperature are defined, the engineer is faced with the selection of a number of parameters which will determine the overall effectiveness of the process. Variables include reactor diameter, reactor length, pressure, liquid rate, gas rate, gas/liquid stoichiometry, catalyst particle size, catalyst particle shape, catalyst loading density, number of vessels, heat removal method, among others.

Undaunted by the complexity of the system, there have been numerous attempts in the past to optimize reactor operation and/or design using selected variables. Some limited successes have been claimed for certain types of chemical reactions and/or using certain flow regimes.

U.S. Pat. No. 4,288,640 describes cocurrently passing a gas and liquid through a packed column in the form of a turbulent stream at rates such that, when the gas flow rate is kept constant, a variation in flow rate of the liquid produces a rise in the pressure difference $\Delta p$ with increasing liquid flow load L, expressed as $\Delta p/L$, at least twice as large as the rise $\Delta p/L$ under liquid trickling conditions providing laminar flow of the liquid over the packing bodies and continuous gas flow but the liquid flow rate being below the rate at which pulsing $\Delta p$ in the column is produced, using specified packing.

U.S. Pat. No. 5,081,321 describes a catalytic hydrogenation process to produce isopropanol by feeding hydrogen gas and acetone into a fixed bed reactor forming a cocurrent gas-liquid downflow while maintaining the catalyst bed in a trickle bed state, wherein the following equation is met: $\{B/[A \cdot (\sigma/100)]\} > 1$, wherein B is moles of hydrogen, A is moles of acetone, and $\sigma$ is percent conversion of acetone, provided that a trickle flow state is maintained.

U.S. Pat. No. 5,093,535 teaches a cocurrent hydrogenation process having a hydrogenation zone containing a bed of catalyst whose particles lie in the range of 0.5 mm to 5 mm and maintaining the supply of feedstock to the bed so as to maintain a superficial liquid velocity of liquid down the bed in the range of from about 1.5 cm/sec to about 5 cm/sec while controlling the rate of supply of the $H_2$-containing gas to the bed so as to maintain at the top surface of the bed of catalyst particles a flow of $H_2$-containing gas containing from 1.00 to about 1.15 times the stoichiometric quantity of $H_2$ theoretically necessary to convert the organic feedstock to the hydrogenation product.

FR 2,597,113 relates to trickle phase method for the selective hydrogenation of highly unsaturated hydrocarbons, the method characterized in that the product used, which contains the highly unsaturated components and the hydrogenation gas, which contains hydrogen, are directed through the catalyst at a surface flow velocity with respect to the geometric surface of the particles of the total quantity of catalyst of $1.5 \times 10^{-7}$ to $3.0 \times 10^{-5}$ m/s relative to the hydrogenation phase.

The prior art methods, however, suffer inter alia by making use of only a very small number of reactor variables available and thus are too restrictive, and/or do not provide results on pilot plant or laboratory scale operations that can consistently be scaled up to commercial scale reactors.

E. Talmor, AIChE Journal, Vol. 23, No. 6, p. 868-874 (November 1977) teaches one type of flow map to describe the flow regimes in downflow through packed beds and found that the flow regimes encountered in such systems depend on the superficial volumetric gas-to-liquid ratio and the ratio of inertia plus gravity forces to viscous plus interphase forces.

Flow maps attempt to predict the flow regime at a given set of measurable conditions, but studies of this sort do not usually make predictions or recommendations as to how well a chemical reaction would occur in the predicted flow regime.

Flow maps have been used in a number of patents to ascertain useful hydraulic regimes (e.g., trickle, pulse, or bubble), e.g., U.S. Pat. No. 6,774,275 (WO2004016714) and the aforementioned U.S. Pat. No. 5,081,321. Numerous other publications concern this subject matter, e.g., Sherman et al., "Kinetic and Hydrodynamic Effects in the Activity Testing of Hydrodesulfurization Catalyst in Packed-Bed Reactors", Symposium, Modeling and Troubleshooting of Commercial-Scale Reaction Systems, AIChE 71st Annual Meeting, Nov. 12-16, 1978; Morsi et al., "Flow Patterns and Some Holdup Experimental Data in Trickle-Bed Reactors for Foaming, Nonfoaming, and viscous Organic Liquids", AIChE Journal, Vol. 24, No. 2, pp. 357-360, March 1978. Talmor-like maps do not per se concern optimal conditions for a fixed bed reactor; they attempt to predict the flow regime. Typically flow maps are designed using water and air and fail when applied to other fluid systems.

Among other references discussing hydraulic conditions or related factors for operating a reactor include: U.S. Pat. Nos. 4,851,107; 6,492,564; and 6,680,414; Holub et al., "Pressure Drop, Liquid Holdup, and Flow Regime Transition in Trickle Flow, AIChE Journal, Vol. 39, No. 2, pp. 302-321, February 1993; Tosun, "A Study of Cocurrent Downflow of Nonfoaming Gas-Liquid Systems in a Packed Bed. 1. Flow Regimes: Search for a Generalized Flow Map", Ind. Eng. Chem. Process Des. Dev. 1984, 23, 29-35; Cheng et al., "Influence of hydrodynamic parameters on performance of a multiphase fixed-bed reactor under phase transition", Chemical Engineering Science 57 (2002) 3407-3413; Stuber et al., "Partial Hydrogenation in an Upflow Fixed-Bed Reactor: A multistage Operation for Experimental Optimization of Selectivity", Ind. Eng. Chem. Res. 2003, 42, 6-13; Al-Dahhan et al., "High Pressure Trickle-Bed Reactors: A Review, Ind. Eng. Chem. Res. 1997, 36, 3292-3314; Moreira et al., "Influence of Gas and Liquid Flow Rates and the Size and Shape of particles on the Regime Flow Maps Obtained in Cocurrent Gas-Liquid Downflow and Upflow through Packed Beds", Ind. Eng. Chem. Res. 2003, 42, 929-936; Attou et al., "A two-fluid hydrodynamic model for the transition between trickle and pulse flow in a cocurrent gas-liquid packed-bed reactor", Chemical Engineering Science 55 (2000) 491-511; Herskowitz et al., "Effectiveness Factors and Mass Transfer in Trickle-Bed Reactors", AIChE Journal, Vol. 25, No. 2, pp. 272-283; Gianetto et al., "Hydrodynamics and Solid-Liquid Contacting Effectiveness in Trickle-Bed Reactors", AIChE Journal, Vol. 24, No. 6, pp. 1087-1104; Worstell et al., "Properly Size Fixed-Bed Catalytic Reactors", Chemical Engineering Progress, June 1993, pp. 31-37; Dudukovic, "Catalyst Effectiveness Factor and Contacting Efficiency in Trickle-Bed Reactors", AIChE Journal, Vol. 23, No. 6, pp. 940-944; Morita et al., "Mass Transfer and Contacting Efficiency in a Trickle-Bed Reactor", Ind. Eng. Chem, Fundam., Vol. 17, No. 2, 1978; Ng et al., "Trickle-Bed Reactors", Chemical Engineering Progress, November 1987, pp. 55-70; Borkink et al., "Influence of Tube and Particle Diameter on Heat Transport in Packed Beds", AIChE Journal, Vol. 38, No. 5, May 1992, pp. 703-715; Talmor, "Part II. Pulsing Regime Pressure Drop", AIChE Journal, Vol. 23, No. 6, pp. 874-878; Sai et al., "Pressure Drop in Gas-Liquid Downflow Through Packed Beds", AIChE Journal, Vol. 33, No. 12, December 1987, pp. 2027-2036; Borio et al., "Cocurrently-Cooled Fixed-Bed Reactors: A Simple Approach to Optimal Cooling Design", AIChE Journal, Vol. 35, No. 11, pp. 1899-1902, November 1989; Satterfield et al. "Mass Transfer Limitations in a Trickle-Bed Reactor", AIChE Journal, pp. 226-234, March 1969; Charpentier et al., "Some Liquid Holdup Experimental Data in Trickle-Bed Reactors for Foaming and Nonfoaming Hydrocarbons", AIChE Journal, Vol. 21, No. 6, pp. 1213-1218, November 1975; and Burghardt et al., Chemical Engineering Science 57 (2002) 4855-4863.

The present inventors have surprisingly discovered a method of reducing the multidimensional problem outlined above to two dimensions.

SUMMARY OF THE INVENTION

The invention relates to a method whereby the numerous variables used to carry out a reaction (or even mass transfer) in a fixed bed reactor can be reduced to, or summarized by, two variables: Ta and $\phi$. In an embodiment, Ta and $\phi$ are used as coordinates. Plotting plural coordinates (Ta, $\phi$) based on a variety of conditions, a graph is obtained from which boundary conditions defining operating conditions for a desired process, such as a chemical reaction or mass transfer, may be determined. In another embodiment, coordinates (Ta, $\phi$) are determined from a complete set of operating parameters and a determination is made whether or not the operating parameters fall within desired boundary conditions.

The present inventors have also surprisingly discovered an optimal hydraulic regime for conducting three-phase reactions or mass transfer in a fixed bed reactor. In a preferred embodiment, the defined hydraulic regime provides a convenient method for design, operation, and/or diagnosis of an hydrogenation process in a fixed bed reactor.

Included within the term "reaction", for the purposes of the present invention, is mass transfer. While the use of a fixed bed comprising a catalyst is contemplated in preferred embodiments, the present invention is applicable also to reactors having a fixed bed of any particulate or granular material which is intended to interact with a liquid and/or gaseous material flowing through said reactor.

The invention is directed, in another embodiment, to the determination of appropriate hydraulic conditions for a fixed bed reactor from a plot of plural (Ta, $\phi$) coordinates, wherein Ta is defined as the sum of the inertia and gravity forces at a preselected point in said reactor divided by the sum of the interface and viscous forces at said preselected point in said reactor, and $\phi$ ("phi") is defined as the gas to liquid volumetric flow ratio at said preselected point in said reactor.

In still another embodiment, a plot of plural (Ta, $\phi$) coordinates is used to provide a reactor or system of fixed bed reactors that meet the requirements of the desired conversion of reactants, supplying an appropriate amount of hydrogen, removing the heat of reaction to control the temperature within the desired range, and ensuring that the hydraulic conditions at a plurality and preferably substantially all of the points in the fixed bed are optimized such that, in a preferred embodiment, the flow is radially uniform and the gas is uniformly dispersed as fine bubbles throughout the length of the reactor.

In a further embodiment, the substantially optimum hydraulics are determined by setting the design variables, such as volumetric gas to liquid ratio, according to the criteria given herein.

In another embodiment, the invention is directed to a fixed bed reactor operating under the following hydraulic conditions:

Ta<N; and (a)

φ>a+(b·Ta); (b)

wherein variables N, a, and b are predetermined for a given reaction from the plot of plural (Ta, φ) coordinates, and Ta is further defined by the following equation:

Ta=(1+1/Fr)/(We+1/Re); (c)

wherein Fr is the Froude number, We is the Weber number, and Re is the Reynolds number. The Froude, Weber, and Reynolds numbers are per se known in the art.

In yet another embodiment, the invention is directed to the design and/or operation of fixed-bed, gas-liquid, downflow hydrotreating process, preferably a hydrogenation process, and preferably operating under one or more of the aforementioned embodiments. In a preferred embodiment the hydrogenation process comprises the hydrogenation of carbonyl moieties, more preferably hydrocarbon species having aldehyde and/or ketone.

It is an object of the invention to provide a method or system for designing, operating, monitoring and/or diagnosing a fixed bed reaction or reactor, particularly a hydrogenation or hydrotreating process or any mass transfer process using a fixed bed reactor.

It is yet another object of the invention to define conditions where the reactor hydraulics allow for maintenance of good gas/liquid contact and mass transfer and thereby provide for more efficient use of hydrogen and/or avoiding the need to recycle large amounts of hydrogen.

These and other embodiments, objects, features, and advantages will become apparent as reference is made to the following figures, detailed description, preferred embodiments, examples, and appended claims.

BRIEF DESCRIPTION OF THE DRAWINGS

In the accompanying drawings, like reference numerals are used to denote like parts throughout the several views.

DETAILED DESCRIPTION

Figure 1:
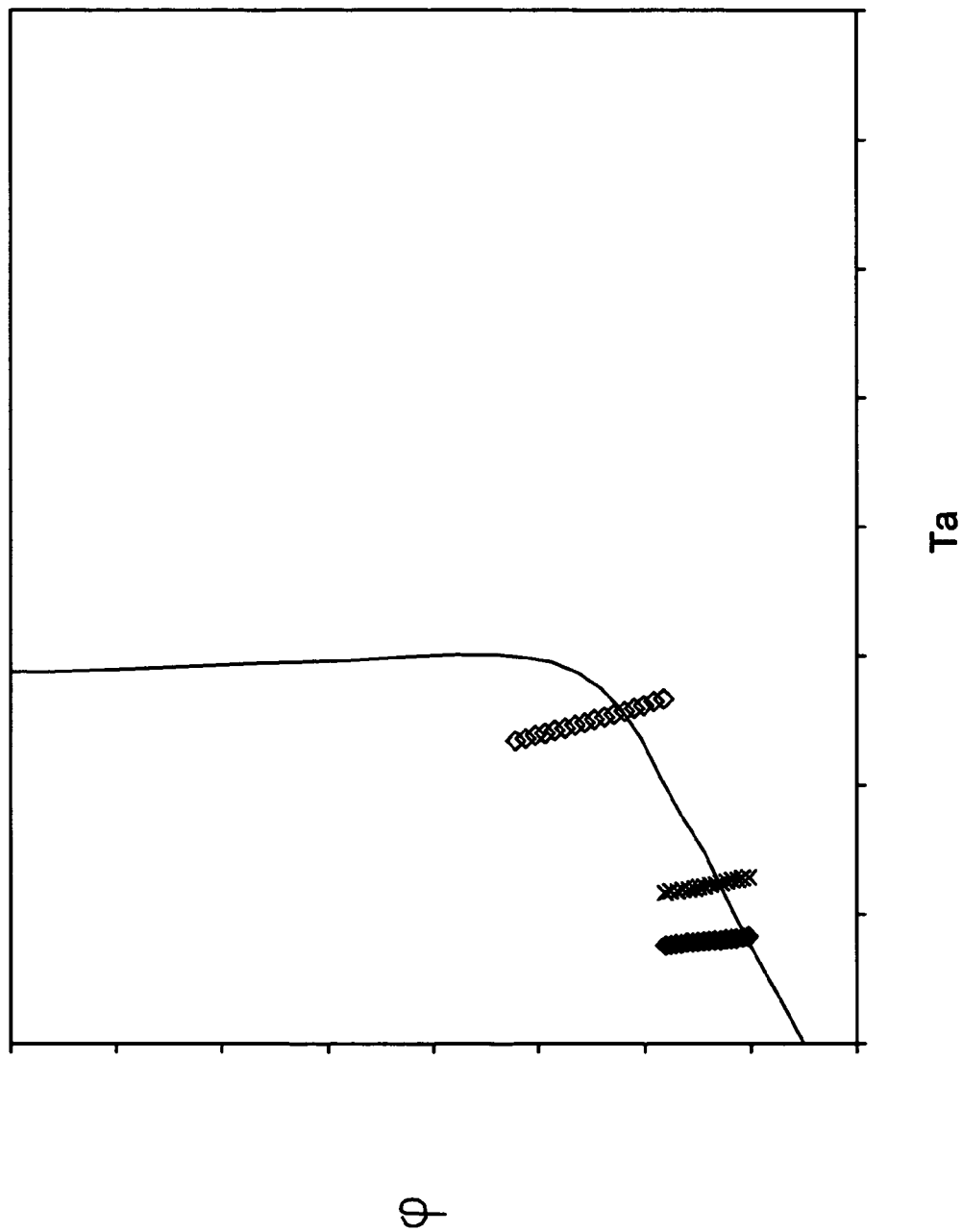
FIG. 1 illustrates plural (Ta, φ) coordinates taken at the inlet and outlet within a reactor in an embodiment of the invention.

The present invention may be characterized, in an embodiment, as a reduction of a multidimensional problem to two dimensions: Ta and φ, wherein the variable Ta is defined herein as the sum of inertia and gravity forces divided by the sum of the interface and viscous forces, and the variable φ is defined herein as the volumetric gas to liquid ratio. Appropriate reactor conditions for a fixed bed catalytic reactor may be determined from plural coordinates (Ta, φ), as described in detail below. In an embodiment, appropriate reactor conditions may be determined from an orthogonal (x, y) plot where, for instance, Ta is x-axis and φ is the y-axis.

Ta may be further characterized, in an embodiment, by the expression Ta=(1+1/Fr)/(We+1/Re). Each of these expressions will be described in detail below. φ may be further characterized, in an embodiment, by the expression $u_G/u_L$.

The terms in the expression (1+1/Fr)/(We+1/Re) have the meanings set forth in Talmor, AIChE 23, No. 6, pp. 868-873, discussed in the Background section, above, i.e, Fr is the Froude number, We is the Weber number, and Re, the Reynolds number, are terms of art having well-defined meanings as set forth in the aforementioned Talmor article, and which may be determined by one of ordinary skill in the art.

The parameters in the aforementioned expressions are defined as follows:

$Fr=[(L+G)v_{LG}]^2/gD_h$ $We=D_h(L+G)^2 v_{LG}/\sigma_L$ $Re=D_h(L+G)/\mu_{LG}$ $v_{LG}=(L/G)v_L/(1+L/G)+v_G/(1+L/G)$ $\mu_{LG}=(L/G)\mu_L/(1+L/G)+\mu_G/(1+L/G)$ $D_h=2\epsilon D/[2+3(1-\epsilon)(D/D_p)]$ where
D=column diameter, m
$D_h$=bed hydraulic diameter, m
$D_p$=equivalent particle diameter of catalyst, m
Fr=Froude number, unitless
G=superficial mass velocity of gas, kg/m²s
g=acceleration due to gravity, m/s²
L=superficial mass velocity of liquid, kg/m²s
Re=Reynolds number, unitless
$u_G$=ideal superficial velocity of gas at reactor temperature and pressure, m/s
$u_L$□=superficial velocity of liquid, m/s
We=Weber number, unitless
$\epsilon$=void fraction of catalyst bed, unitless
$\mu_G$=viscosity of gas, kg/ms
$\mu_L$=viscosity of liquid, kg/ms
$\mu_{LG}$=effective viscosity of the gas-liquid mixture, kg/ms
$\rho_G$=ideal gas density at reactor temperature and pressure, kg/m³
$\rho_L$=liquid density, kg/m³
$\sigma_L$=liquid surface tension, N/m
$v_G$=ideal specific volume of gas at reactor temperature and pressure, m³/kg,
$v_L$=specific volume of liquid, m³/kg
$v_{LG}$=specific volume of the gas-liquid mixture, m³/kg For spherical catalyst shape, $D_p$ is the diameter of the sphere, and for non-spherical catalyst geometry, the equivalent particle diameter is calculated from the volume of the particle in cubic meters, $V_p$, and the external surface area of the particle in square meters, $A_p$, according to the equation $D_p=6V_p/A_p$.

In an embodiment, appropriate reactor conditions for a fixed bed catalytic reactor may be determined from a plot of plural coordinates (Ta, φ). By way of example, a chemical process is carried out under predetermined conditions in fixed bed catalytic reactor and the values Ta and φ for each predetermined condition is plotted on a graph as coordinates (x, y)=(Ta, φ). It will be understood by one of ordinary skill in the art that the coordinates may also be plotted in numerous ways, such as (x, y)=(φ, Ta), using a three-dimensional plot by adding another variable, and so on. It will be further understood by the same artisan that a physical plot is not necessary, but rather a computer program may be written to determine appropriate boundary conditions and/or whether or not a given set of coordinates (Ta, φ) fall within predetermined boundary conditions.

The term "predetermined" as used herein means "determined or selected beforehand".

In an embodiment, an indication is made on the graph regarding whether the results obtained are satisfactory or not. Whether or not conditions are satisfactory or not can be determined by one of ordinary skill in the art. It may be a subjective determination or an objective determination or a combination thereof. Acceptable operating conditions may mean, by way of example, that part of a reactor is operable and not subject to hotspots or runaway, and some larger part of the reactor is operating in the optimal regime.

Conditions are varied so that a number of results are obtained, which may include both satisfactory and unsatisfactory experimental results, so that a plot of plural (Ta, φ) coordinates for a given chemical reaction within a given reactor (or multiple reactors in series, parallel, or a combination thereof) having a fixed bed. In an embodiment, variables for changing conditions include one or more of the following: reactor temperature, reactor diameter, reactor length, pressure, liquid rate, gas rate, gas/liquid stoichiometry, catalyst particle size, catalyst particle shape, catalyst loading density, catalyst bed void fraction, number of vessels, presence or absence of recycle and recycle stoichiometery (e.g., presence or absence of $H_2$ in recycle, presence or absence of product recycle), and heat removal method. Variations on heat removal method include: adiabatic, recycle with external cooling, recycle injected in one or more points of the reactor, coils or tubes within the catalyst bed, and mixtures thereof.

The coordinates (Ta, φ) may all be determined at the same point within the reactor, e.g., at the reactor inlet for cocurrent flow, but more preferably coordinates (Ta, φ) are determined for numerous points within the reactor, e.g, reactor inlet and reactor outlet and at one or more points in the bed, in order to optimize the reactors performance in producing product.

A boundary line that differentiates good from bad results will become apparent from the plot of plural coordinates (Ta, φ) to one of ordinary skill in the art. Thus, it has surprisingly been found that plural coordinates (Ta, φ) map out an orthogonal space, with "good" or optimum points falling in a distinct region and "bad" or inoperable points falling in another distinct region, with "marginal" or operable points falling in yet another separate region between the optimal and inoperable regions. The user may select more refined differentiation of the coordinates, e.g., optimum and suboptimum, or good, operable, not operable, and so on. Such characterization is fully within the skill of the ordinary artisan in possession of the present disclosure. The boundary line(s) defining desired operating regions may be determined qualitatively or it may be determined quantitatively, such as by a determination of a boundary defined by a slope, y-intercept, and appropriate operating conditions may include other boundary conditions, as discussed below in the examples. Preferred operating conditions for a hydrogenation reaction in a fixed bed catalytic reactor according to the present invention include that the hydraulic conditions at a plurality and preferably substantially all of the points in the fixed bed are optimized such that the flow is radially uniform and the gas is uniformly dispersed as fine bubbles throughout the length of the reactor.

Figure 3:
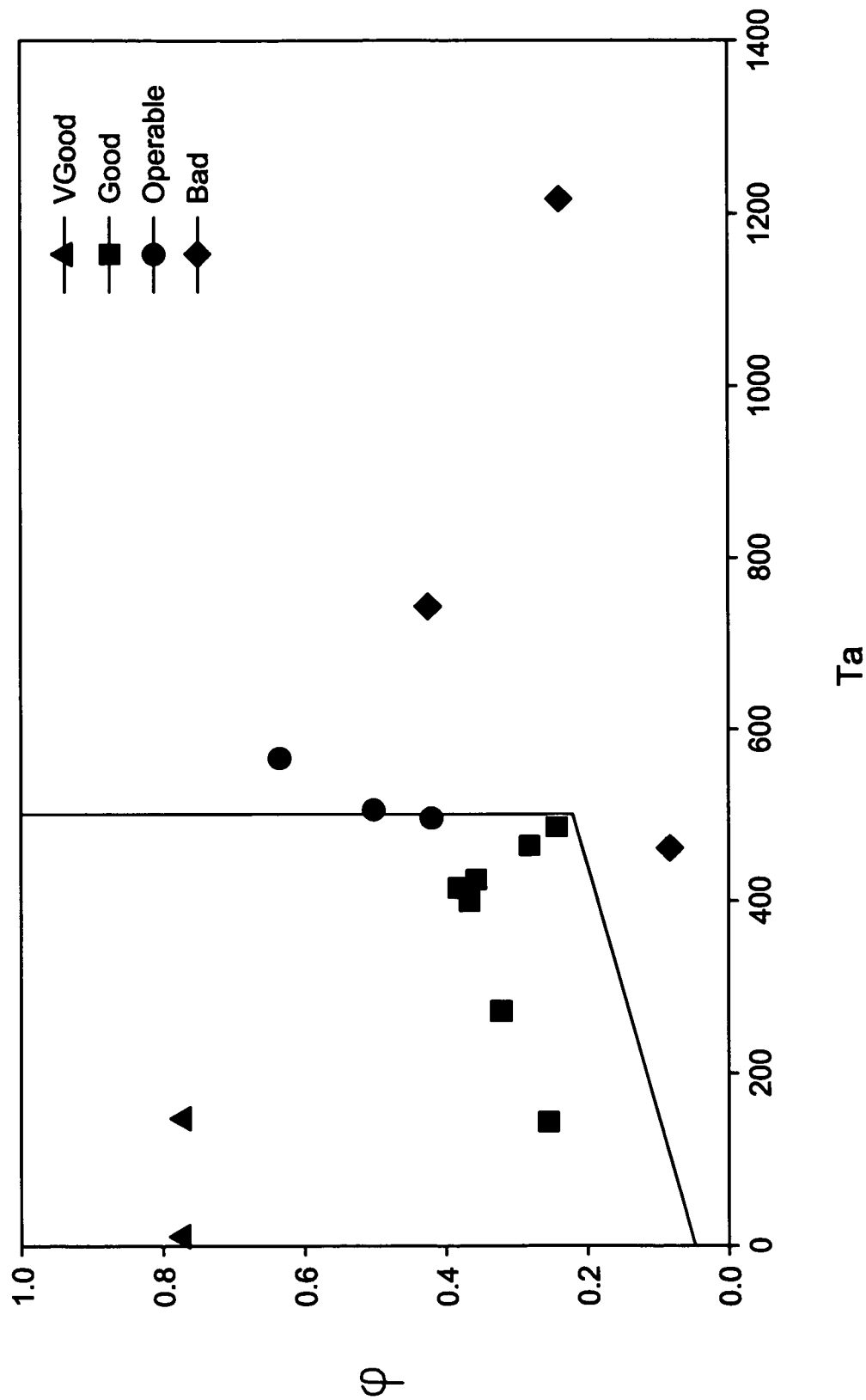
FIG. 3 illustrates a plot of Ta versus (p for an embodiment of the invention.

Boundary conditions may be assigned to preferred operating conditions. By way of example, according to an embodiment of the invention, a fixed bed reactor is operated under the following hydraulic conditions: (a) Ta<N; and (b) φ>a+ (b·Ta), wherein, in addition to Ta and φ, the variables N, a, and b are predetermined for a given reaction. The parameters N, a, and b are predetermined from a plot of φ versus Ta, as stated previously. As will be apparent to one of ordinary skill in the art in possession of this disclosure, in the equation φ>a+ (b·Ta), the term "a" is the y-intercept and the term "b" is the slope for a boundary line drawn, as shown in FIGS. 1 and 3, and in the equation Ta<N, the term "N" is the limit of Ta determined by the boundary line drawn in these same figures. It will also be apparent to the person of ordinary skill in the art reading this disclosure that more complicated boundary lines and thus more complicated equations may be developed, but one of the advantages of the present invention is its simplification of a complex problem. It will also be apparent to one of ordinary skill in the art in possession of the present disclosure that a physical plot is not necessary but rather a computer program could be written and used to define a set of fully defined boundary conditions using the parameters Ta and φ as set forth herein.

In an embodiment, Ta is less than about 600 or more preferably less than about 500. In another embodiment, Ta is greater than about 10. In yet another embodiment, Ta is greater than about 10 and less than about 500, or less than 600.

In a preferred embodiment φ<0.8. In another preferred embodiment φ<1.1. In yet another preferred embodiment, the only limit on φ is that the reactor operate in the bubble flow regime, which may be determined by routine experimentation by one of ordinary skill in the art in possession of the present disclosure.

In another preferred embodiment, the reaction conditions are maintained according to the following hydraulic conditions:

$$10 < Ta < 500; \text{ and} \tag{a}$$

$$\{0.045 + (0.00035 \cdot Ta)\} < \phi < 0.8 \tag{b}$$

In an embodiment, reactor hydraulic conditions, expressed by one or more of the above embodiments, will hold in a plurality of points in said reactor, preferably wherein conditions are sufficient to allow for a chemical reaction to occur, and more preferably in the entirety of said reactor.

In an embodiment, the conditions in a reactor may be monitored and maintained under the aforementioned hydraulic conditions, so that the desired product is obtained and flow is radially uniform and the gas is uniformly dispersed as fine bubbles throughout the length of the reactor.

In an embodiment, if conditions drift or otherwise are determined to be outside of the hydraulic conditions according to the invention, then at least one of temperature or pressure should be modified so as to obtained the desired hydraulic conditions. If this does not provide the desired results, then one of more of the following should be modified: changing the composition of at least one of the gaseous or liquid feeds (e.g., adding diluents such as inert gases or liquids, partially recycling product, adding more reactant gas and/or liquid, adding surfactants, and the like), catalyst bed particle size or shape, or catalyst bed void fraction, or diameter, length and/or number of beds, or a combination of these parameters. It will be recognized that a temperature range, pressure range, and catalyst composition are usually determined based on chemistry and pilot plant data prior to the design of the commercial reactor, which places a practical limit on the preferred options.

Pressure (or gas density) and temperature remain the key or preferred hydraulic parameters that may be adjusted in meeting the conditions of the present invention. The other preferred hydraulic variables are catalyst particle size and shape, liquid velocity, gas velocity, and bed void fraction.

The effects of bed void fraction may be conveniently determined by extrapolation based on first principles and visual observations in a transparent laboratory reactor using water and air. Combinations of two or more of the preferred hydraulic variables—catalyst particle size, liquid velocity, gas velocity, pressure, or a combination thereof—are also preferred embodiments of the present invention.

In a preferred embodiment the reaction is a hydrotreating proceess, preferably a hydrogenation process, more preferably comprising the hydrogenation of carbonyl moieties, still more preferably the hydrogenation of hydrocarbon species having aldehyde and/or ketone moieties and yet still more preferably the hydrogenation process comprises the hydrogenation of aldehydes and/or ketones produced in the Oxo Process, more yet again more preferably such a process using an Oxo hydrogenation catalyst, said catalyst in the form of extrudates which, in one embodiment, have from about 1 to about 4 mm nominal diameter with a length to diameter ratio of about 3 or more, in another embodiment have a trilobed or quadralobed shape, and in a still yet more preferred embodiment have the aforementioned diameter and shape.

The invention is not specific to any particular reaction or catalyst. It is specific, however, to fixed bed reactors having three phases: the solid phase comprising a fixed bed catalyst, a liquid phase, and a gas phase. Thus, the actual chemical reaction occurring within the system may be, for instance, an hydrogenation reaction, a hydrodesulfurization reaction, a water treatment process, and the like. The invention is particularly beneficial in the design, operation, and diagnosis of a three-phase reaction in a fixed bed reactor having a catalyst therein, providing a convenient tool to increase gas-liquid-catalyst interaction over the full length and diameter of the reactor.

In a more preferred embodiment wherein the chemical reaction is an hydrogenation process comprising the hydrogenation of aldehydes and/or ketones to alcohols, the process of the invention preferably operates always in the dispersed bubble flow regime in a cocurrent downflow scheme. In regimes other than cocurrent downflow operating under substantially dispersed bubble flow regime, the axis of the map provided by Ta versus $\phi$ may need to be modified to account for different forces acting on the fluids, as would be recognized by one of ordinary skill in the art in possession of the present invention (bearing in mind that number Ta has been previously defined broadly as the inertia and gravity forces divided by the interface and viscous forces). Nevertheless the present invention provides a good starting point for optimizing conditions under different hydrodynamics than this preferred embodiment.

Thus, in a preferred embodiment, the hydrogenation process is operated under conditions sufficient to provide for bubble flow regime.

Various embodiments as set forth herein, preferred and otherwise, may be combined as would be readily apparent to one of ordinary skill in the art in possession of the present disclosure. Thus, for instance, in a further embodiment, which is a preferred embodiment, the present invention may be applied to a cocurrent downflow hydrogenation process under conditions sufficient to provide for dispersed bubble flow, and further characterized by the following conditions:

$10 < Ta < 500$, and (a)

$\{0.045 + (0.00035 \times Ta)\} < \phi$ (b)

and in a yet more preferred embodiment wherein $\phi$ is less than 1.1, or less than 0.8.

In a more preferred embodiment, the aforementioned hydraulic conditions are met in at least one three-phase reaction zone wherein the hydrogenation reaction is the hydrogenation of hydrocarbons selected from C3-C20 hydrocarbons and mixtures thereof, wherein at least some of said hydrocarbons have reactive carbonyl moieties. In an embodiment of this more preferred embodiment, the solid phase comprises the fixed bed catalyst which includes a hydrogenation catalyst, e.g., a catalyst selected from cobalt supported on alumina, molybdenum (Mo) supported on alumina, cobalt and molybdenum supported on alumina, nickel and molybdenum supported on alumina, all of the above either reduced or sulfided, and Cu, Cr, Zn, and mixtures of aforementioned catalysts. The liquid phase comprises the C3-C20 hydrocarbons having reactive carbonyl moieties, e.g., aldehydes and/or ketones, and the gas phase comprises a source of hydrogen, e.g., $H_2$. In another embodiment, there may be multiple reactors, which may be a series of reactors or reactors in parallel, or a combination thereof, with the catalyst for each bed independently selected. Also, even more preferably, there may be different layers in the bed, each layer being of a different particle size catalyst and/or loading density. This is particularly useful when gas depletion occurs due to reaction, and the flow conditions need to be adjusted.

In the aforementioned embodiment involving multiple reactors, it is contemplated that either a single graph comprising plural plots of (Ta, $\phi$) coordinates may be prepared for the entire system of plural reactors or plural graphs of plural plots of (Ta, $\phi$) may be prepared, for instance, with a separate graph for each separate reactor.

In an embodiment of the above-recited preferred embodiment, the liquid phase comprises at least one aldehyde and/or ketone selected from C3-C20 aldehydes and/or ketones, preferably C6-C14 aldehydes and/or ketones, and more preferably C8-C13 aldehydes or ketones. Typically the liquid phase feed will be a mixture of aldehydes and/or ketones having a range of carbon numbers and/or a isomers within a single carbon number. A still more preferred embodiment of each of the aforementioned embodiments, the particular range of aldehydes and/or ketones comprises aldehydes and/or ketones made in the Oxo aldehyde process, wherein olefins are reacted under hydroformylation conditions to yield the corresponding aldehyde having one more carbon atom, as discussed in the Background section.

As previously mentioned, the present invention may also be used in reactor design, operation, and/or diagnosis. By way of example, the hydrogen rate (or in the more general case, the gas velocity) may be selected at the desired stoichiometry and then the reactor diameter is selected to provide the preferred liquid velocity within a predetermined graph comprising plural (Ta, $\phi$) coordinates. An option in the design and/or operation may then be selected to include recycling partially converted product to make up part of the liquid feed.

By way of further example, a plot of (Ta, $\phi$) coordinates may be used in the diagnosis or selection of operating conditions, as illustrated in FIG. 1. In FIG. 1, each string of points represents plural coordinates plotted for $(x, y) = (Ta, \phi)$ which are measured at the reactor inlet and outlet (top and bottom points, respectively) and predicted for intermediate points throughout the reactor. In this example, all conditions are kept constant except catalyst particle size and gas flow, i.e., effecting $D_p$ (equivalent particle diameter of catalyst), G (superficial mass velocity of gas), and $u_G$ (superficial velocity of gas), in the equations discussed above. Coordinates representing inoperable conditions are not shown on the graph. The solid line in FIG. 1 representing the boundary conditions, is drawn through each string (and numerous other strings and points not shown on the graph) at approximately the point where performance is judged to be marginal. These points within a reactor where performance deviates from the acceptable conditions may be determined by various tests, such as those discussed herein. Appropriate operating conditions are represented on the graph by any point to the upper left of the solid line representing the boundary conditions. FIG. 1 is intended to illustrate the invention schematically; the actual numbers associated with the graph are not germane to the example.

It should be noted that the present inventors have simplified the method by using the ideal gas phase density $\rho_G$ rather than try to use the actual gas density inside the reactor, which would require taking account of the flashing of volatile components. This is a minor correction which simplifies the effort. In addition, by taking a sample of liquid in and out of the reactor, the amount of $H_2$ consumed at any longitudinal point in the reactor may be determined, and thus the phase ratio at any longitudinal point may be calculated. Likewise, in the preferred embodiment illustrated in FIG. 1, different size particle of catalyst ($D_p$) and void fraction ($\epsilon$) were used, and of course account is taken of this fact for every longitudinal point studied in the reactor.

In an embodiment of the invention, starting point values of physical properties for a process comprising hydrogenation of an organic feedstock in a downflow, cocurrent, fixed bed used in computations herein are as follows: $\mu_G=1.6\times10^{-5}$ kg/m–s; $\mu_L=2.9\times10^{-4}$; $\rho_G=12.3$ kg/m$^3$; $\rho_L=781$ kg/m$^3$; and $\sigma_L=0.015$ N/m. For such a system, values of various parameters will typically vary as follows: column diameter (D) from 0.4 to 2.0 m; particle diameter ($D_p$) from 1 to 3 mm; superficial liquid velocity $u_L$ from 0.005 to 0.04 m/s; superficial ideal gas velocity $u_G$ from 0.001 to 0.01 m/s; and catalyst bed void fraction ($\epsilon$) from 0.38 to 0.54.

While in an embodiment optimal operating conditions specified by the present invention will exist in all parts of the reactor, from the inlet, through all levels in the catalyst bed, to the outlet, in other embodiments only a portion of the reactor will have the specified hydraulic conditions, i.e., a plurality of points in said reactor. One may, for example, choose to have part of a reactor operating in a regime that is merely "operable" but not subject to hotspots or runaway and some larger part of the reactor operating in the "optimal" regime.

The present invention has been described generally above with reference to certain embodiments. The following specific examples are provided as representative examples and are not intended to limit the invention.

EXAMPLES

The following examples describe experiments using commercial reactors in Oxo aldehyde hydrogenation service. The examples illustrate how the present invention may be used to select a range of preferred and/or optimal conditions for a selected reaction.

Testing was done on three commercial reactors. The effects on reactor performance of pressure, gas rate, liquid rate, and particle size were measured by static and dynamic test methods. The performance was measured by analysis of sample, overall heat balance, radial temperature profiles, axial temperature profiles, and dynamic temperature response to temperature pulses, and/or temperature steps under both reacting and non-reacting conditions.

The results of each test were evaluated based on at least two of the above diagnostic methods, and were judged qualitatively to be one of three possible categories: (1) good—the reactor performs as it was designed, is predictable and stable; (2) operable—the reactor can be run safely and continuously, but it is not performing up to its design basis based on low activity, under-utilization of the full length of the bed, poor dynamics, or some other reason; or (3) not operable—some part of the reactor is not responsive or is highly sensitive to one or more of the manipulated variable that an operator may use to set his operating conditions, which may include a hot-spot, cold spot, and the like. In reality there is a continuum of performance definitions across regimes (1) and (2), but they were not qualified further. The boundary line drawn between the good points (1) and the operable points (2) thus shows the boundary criterion for the effective design and operating conditions for fixed bed reactors operating as hydrogenation reactors for Oxo aldehyde hydrogenation. The inoperable points are left as a subset of the operable, or "just operable" points.

Each of three commercial Oxo aldehyde hydrogenation reactors were fitted with multiple thermocouples arranged from the inlet, through the reactor bed, to the outlet. Reactors A, B, and C are fixed beds having a water jacket for protection of vessel integrity in case of emergency. The reactors are essentially adiabatic. Reactors A and B have the capability of recycling partially converted material from the reactor outlet. Reactor C does not have recycle capability. In all of the examples that follow, physical properties of gas and liquid are effectively constant.

Example 1

Gas and liquid rates were varied in an attempt to render inoperable reactors operable. The liquid rate to reactor A was increased by about 30% by decreasing the aldehyde feed and increasing the amount of recycle, and the gas rate was reduced by about 75%, still at about a 60% molar excess to the aldehyde content of the fresh feed. Reactor A was inoperable as the automatic shutdown system was activated due to high temperature. The (Ta, φ) coordinates for this example are (462, 0.083). A similar experiment was run on reactor B. The gas rate was increased and the liquid rate was reduced to such an extent that the high temperature shut down system was activated. The (Ta, φ) coordinates for this inoperable condition were (1216, 0.24).

Example 2

This example compares the performance of reactor C with reactor A, each having different size catalyst particles. Reactor C is 63% of the cross sectional area of reactor A. The catalysts in each reactor is the same, a proprietary catalyst supported on commercially standard extruded supports. They differ only in particle size: Reactor C uses 1.1 mm equivalent diameter catalyst while Reactor A uses 2.1 mm equivalent diameter catalyst. Both reactors are fitted with a water jacket where tempered water, somewhat cooler than the average reactor temperature, is circulating. The water jackets are used to protect the vessel from undetected hotspots that could melt through the reactor wall. The jackets do not remove a significant amount of reaction heat since the reactor diameters are relatively large. Under ideal flow conditions, there should be no significant radial temperature gradient in the reactors. If a significant radial temperature gradient is measured in the bottom of the catalyst bed, it can be averaged over the total cross sectional area of the bed to give a prediction of the temperature of the total reactor effluent in the outlet pipe. If the predicted value and actual value are different, one can determine an appropriate radial mass flow distribution, which, if used in the temperature profile averaging process, gives the actual temperature of the reactor effluent. Since the reactors are liquid full and operate in the dispersed bubble flow regime, the radial mass flow distribution is essentially the liquid flow distribution. This is the method by which the quality of flow distribution was measured in this and other of the examples below.

In Example 2, reactor A was run with a higher superficial liquid mass rate than reactor C by 22%. Reactor A was run with a higher gas superficial mass rate than reactor C by 38%. Both reactors were maintained at essentially the same temperature and pressure; only the velocity of the liquid and gas were varied. The hydrogen rates correspond in both reactors to at least 60% molar excess with respect to the molar amount of aldehyde in the feed to each reactor.

The Talmor map coordinates (Ta, $\phi$) for reactors A and C are (500, 0.42) and (400, 0.37), respectively.

At these conditions, the centerline bed outlet temperature of reactor A was 18° C. higher than the temperature of the mixed reactor effluent in the outlet pipe two meters downstream. The radial temperature difference between the bed centerline and the wall region was 35° C. The apparent activity of the catalyst in reactor A, as measured by sample, was less than the design value. Reactor C showed a relatively flat radial temperature profile and a low temperature difference between the bed bottom and the outlet pipe. Results of the temperature measurements indicated that reactor A had a radial mass flow maldistribution such that the liquid flowing near the wall was 3 to 4 times higher than the flow in the center of the reactor. By the same method of analysis, reactor C had a relatively uniform flow distribution. The smaller particle size improved the performance of reactor C even at lower flow rates per unit area of liquid and gas. The performance of reactor C was classified as "good" and the performance of reactor A was classified as only "operable" based on the measurements at the bottom of the catalyst bed.

Example 3

Figure 2:
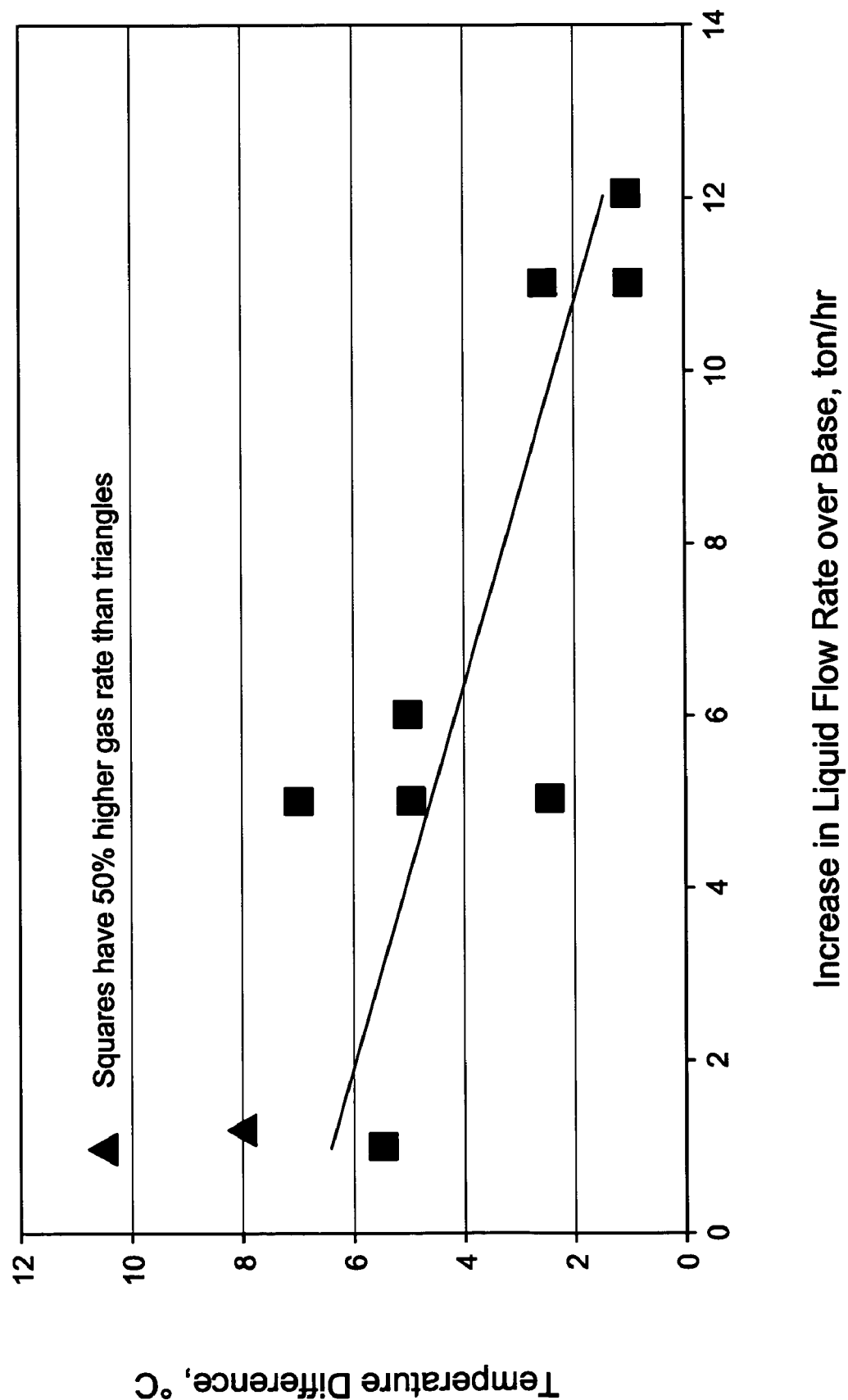
FIG. 2 illustrates the effect of changing a reactor variable for an embodiment of the invention.

Commercial reactor C, an adiabatic reactor, fitted with a water jacket (for safety concerns) and containing 1.1 mm equivalent diameter catalyst, was tested at different liquid and gas flow rates, as shown in FIG. 2. The progression of the reaction down the catalyst bed causes an increase in the axial temperature profile measured near the center of the bed. The relative uniformity of the flow distribution in the reactor was determined by comparing the centerline temperature at the bottom of the bed with the mixed effluent temperature. The mixed effluent temperature provides a measure of the total temperature conditions in the entire reactor. Thus, as the difference between the centerline temperature at the bottom of the bed and the mixed effluent temperature approaches zero, the liquid and gas distribution in the reactor is closer to being uniformly radially distributed, ensuring that there are no significant zones of low flow with the possibility of hot spots or hydrogen starvation. Uniform liquid flow is indicated when the $\Delta T$ is 1-2° C.

The impact of both liquid and gas rate are shown in FIG. 2. The reactor performance is considered to be "good" with a $\Delta T$ less than about 4° C. Each point is plotted as a (Ta, $\phi$) coordinate in FIG. 3. This set of experiments indicates that the reactor has very poor packing distribution which causes temperature maldistribution, and may be brought into good operation by increasing the mass flow (one or both of liquid rate and gas rate) and/or decreasing bed void fraction. Increasing mass flow would typically be adopted in the case where a commercial reactor was operating, whereas decreasing bed void fraction, and/or particle size, and/or changing reactor size typically might be adopted in the design of a reactor.

Example 4

This test illustrates an alternate or supplemental diagnostic method to confirm that the hydrogenation process was operating in the desired hydraulic regime. A pulse increase in the feed temperature was introduced into reactor A of Example 2 and at the same operating conditions as Example 2. At arbitrary time 6.5, the steam valve on the feed temperature conditioning control system was opened for approximately one unit of time to allow the reactor feed temperature to increase by 5° C. At that time, the temperature controller was put into automatic at the original setpoint. The temperature responses down several axial positions of the reactor were recorded by means of the reactor thermocouples and standard plant instrumentation, as shown in FIG. 4.

Figure 4:
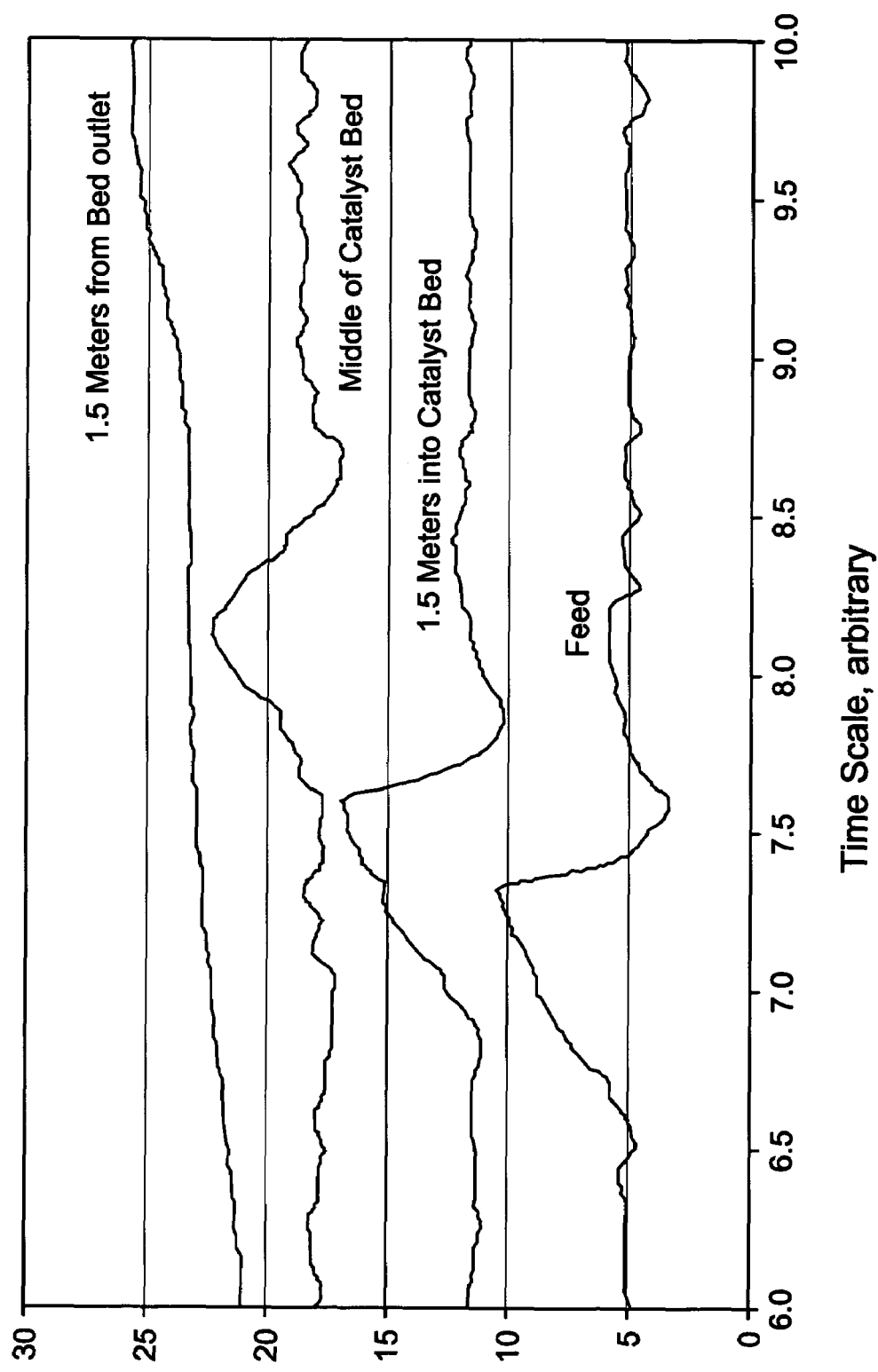
FIGS. 4, 5, and 6 illustrate the effect of a temperature pulse at various points in a reactor for an embodiment of the invention.

FIG. 4 shows the feed temperature, a catalyst bed temperature 1.5 meters from the inlet distributor, a temperature in the middle of the bed, and a temperature 1.5 meters from the outlet of the bed. The shapes and delay times of the first two thermocouples are in line with what would be expected from a catalyst bed with well distributed uniform flow across the cross section of the reactor. Near the bottom of the bed, there is not enough flow over the last thermocouple to change its temperature significantly. Radial temperature measurements showed this reactor to have about 4 times the liquid velocity near the wall region than at the center-line. The consumption of gas in passing through the reactor has depleted the gas enough to make the bubble flow regime unstable, allowing the gas and liquid to separate into distinct regions. The coordinates of this process condition in terms of (Ta, $\phi$) are given in Example 2.

Example 5

Figure 5:
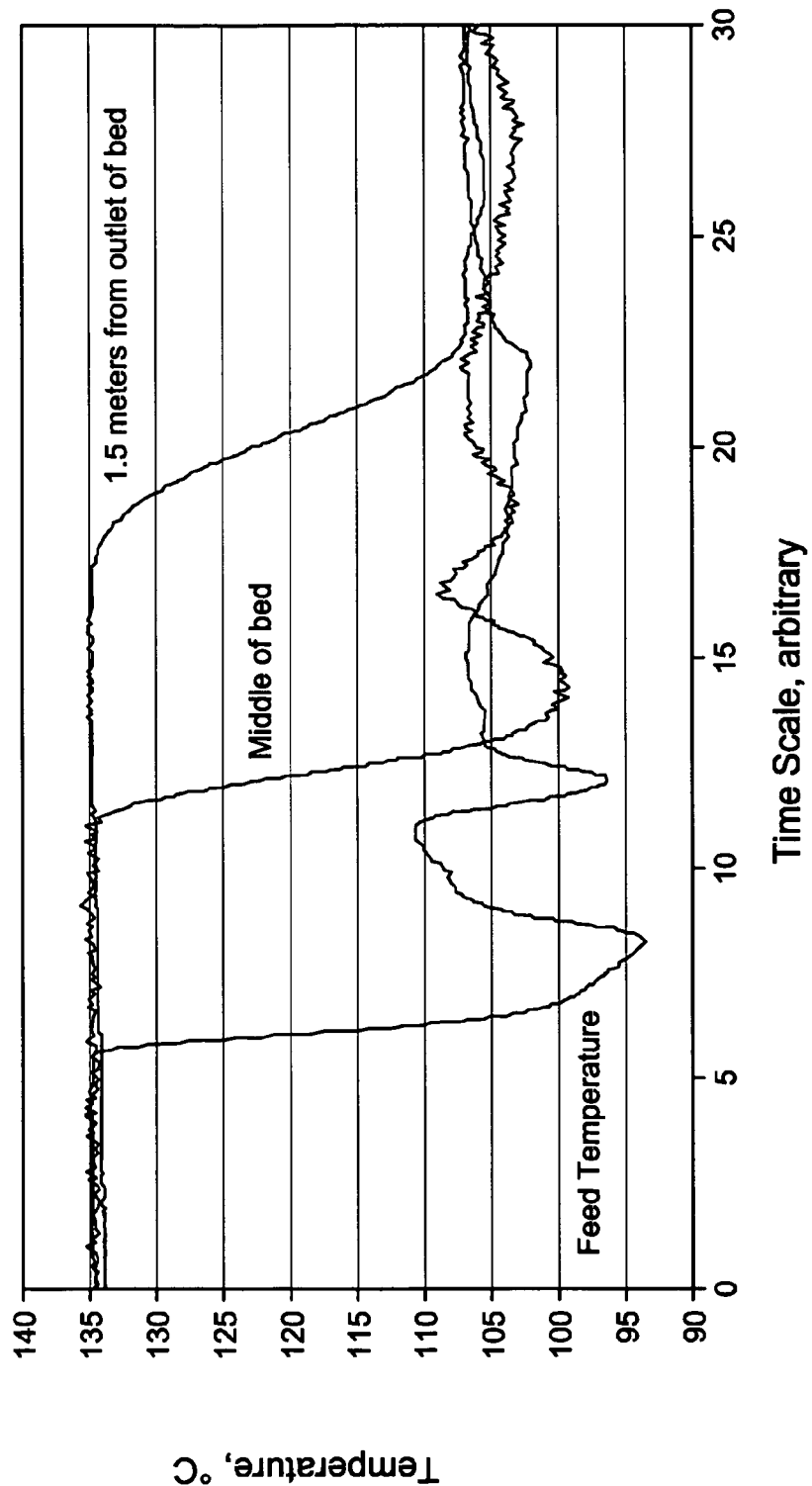
Figure 6:
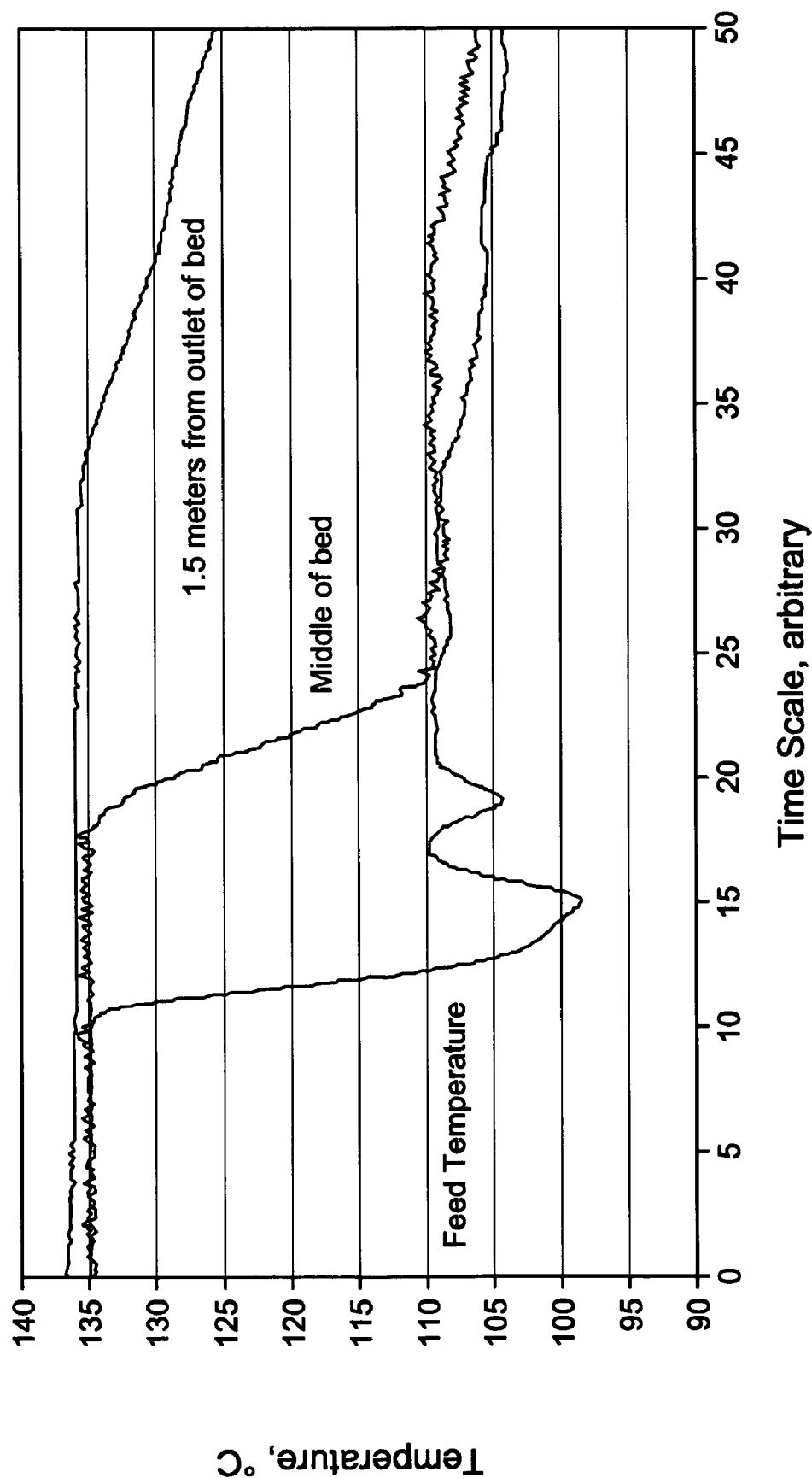

Dynamic testing of two reactors type A under recirculating/no reaction condition are illustrated in FIGS. 5 and 6.

Reactor A was tested with circulation of fully converted liquid and no fresh feed. Clearly, there is no consumption of gas as the two phases travel down the reactor. Initially the reactor was at 135° C. when, at time 5, the set point on the feed temperature was reduced by 30° C. The transient response of all the axial temperature measurements were recorded. Two tests were done at constant liquid flow rate. FIG. 5 illustrates the axial temperature response to step change in feed temperature at high gas rate and FIG. 6 illustrates the axial temperature response to step change in feed temperature at low gas rate. The gas rate in FIG. 5 is 3.5 times the gas rate in FIG. 6. At the higher gas rate, it can be seen from FIG. 5, the temperature responses from top to bottom of the reactor are nearly identical (and thus nearly ideal), indicating that the flow is near plug flow and the liquid distribution remains uniform across the cross section of the reactor.

As shown in FIG. 6, the dynamic response of middle of the bed temperature is similar to that of the higher gas rate example, indicating that the initial distribution of liquid and gas has been maintained for a certain distance into the reactor. The thermocouple nearest the bottom of the reactor does not show the sharp turndown of the previous test, and it falls much more slowly. This indicates that the flow near the center of the bed has slowed down considerably and has migrated toward the reactor wall, most likely with the gas migrating toward the center. The bubble flow regime at these conditions of liquid and gas rate is not stable for the entire length of the reactor.

Since there is no gas consumption, the gas to liquid ratio at all levels in the reactor is the same. The time scales are identical for each of the cases. The (Ta, φ) coordinates of the high gas case are (272,0.32) and for the low gas case are (462,0.08).

Example 6

According to Gupta (supra), a natural tendency for the phase separation exists because the gas and liquid phases flowing separately through different paths in the bed yield a lower pressure drop than when they share the same paths. The following example shows that when the gas is sufficiently depleted by reaction, phase separation occurs. In this case, liquid migrated predominantly to the wall region and consequently, gas holdup increased in the center of the reactor. Example 2 showed low flow in the centerline of the reactor that started below the midpoint of the bed.

At the same flow conditions at which the temperature pulse test was done in Example 4, a steady state radial temperature profile across the catalyst bed was measured. When the temperature profile is averaged over the cross sectional area of the reactor, appropriately weighted by the mass flow rate at each radial position, or, more precisely, in each of the sequential annuli marked by the radial positions, the average temperature can be made to match the mixed effluent from the reactor outlet temperature, assuming a radial mass flow profile. This assumed mass flow profile may be of any arbitrary shape, linear, parabolic, etc. It will be obvious to anyone skilled in the art that if the flow is radially uniform, the values of the flow profile computed to match the average bed temperature with that of the reactor outlet will be relatively constant across the radial direction of the reactor. The simplest profile to choose is a linear one.

Figure 7:
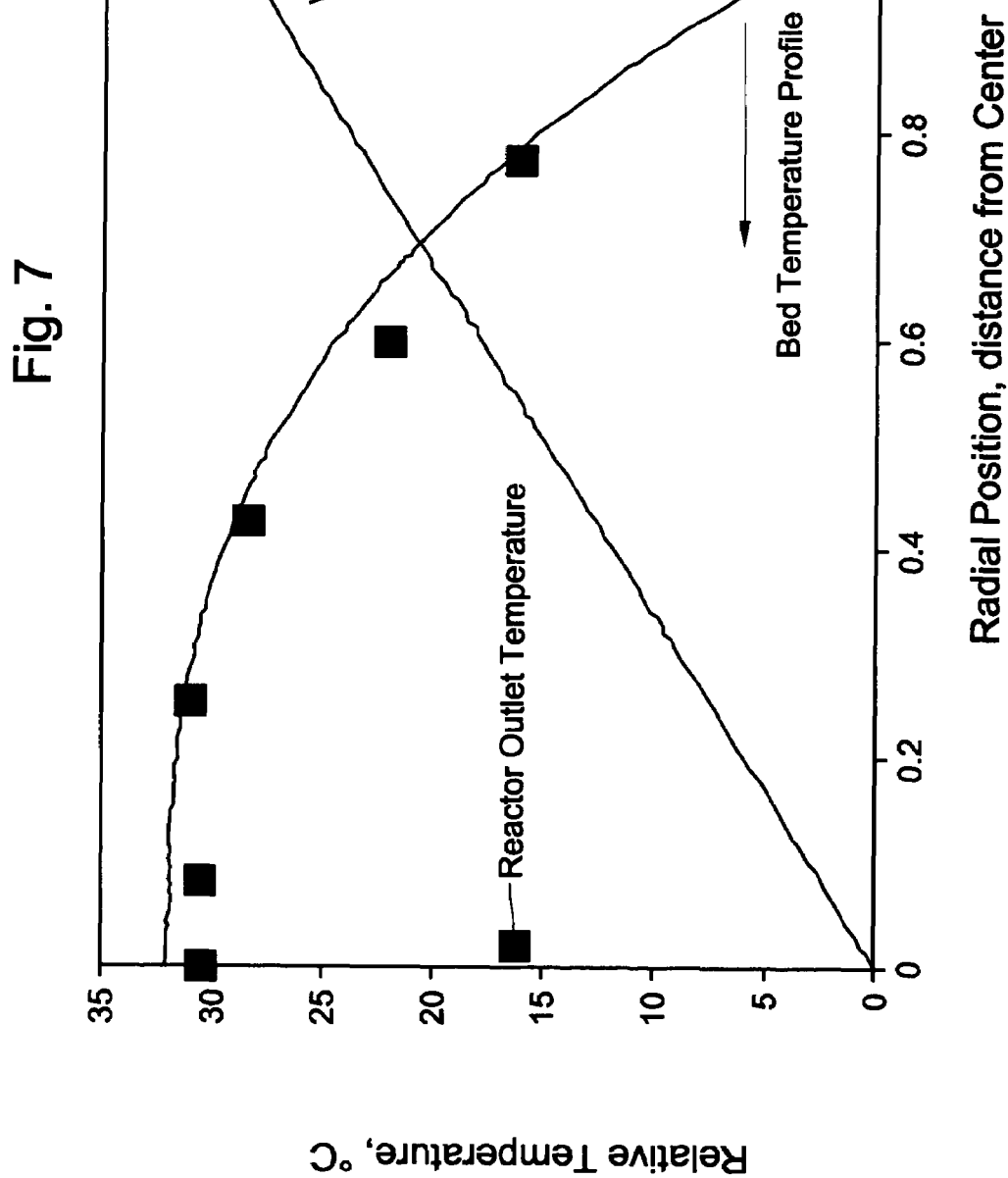
FIG. 7 illustrates a radial temperature profile for an embodiment of the invention.

The radial temperatures are compared with the outlet line temperature in FIG. 7. The linear velocity profile which matches the outlet line temperature with the averaged radial temperatures shows that the mass flowing near the wall to be several times what it is in the center of the reactor. The mass flow is essentially the liquid only flow. The lower temperature near the wall is caused by the loss of adiabatic heating due to the starvation of hydrogen which has most certainly migrated to the center of the reactor.

These examples illustrate the diagnostic methods, which when taken together, unequivocally explain the quality of the three-phase bubble flow regime over the entire length of the reactor, in terms of effectively conducting a hydrogenation reaction. Additional experiments were performed at different conditions, each analyzed using one or more of these diagnostic methods, to develop the optimum operating conditions for a hydrogenation process. These are shown in aggregate in FIG. 3. For this embodiment, boundary conditions for "good" operation are determined to be 10<Ta<500 and {0.045+(0.00035·Ta)}<φ<1.1.

The present inventors have surprisingly found that in a preferred embodiment, process design decisions selected from at least one of: higher liquid velocity, higher gas velocity, smaller catalyst particle size, lower bed void fraction, have the most positive effect on the safe and productive operation of a hydrogenation process. All these factors come with a higher initial investment cost or higher operating cost. A hydrogenation process designed and operated within the conditions of the Ta and φ specifications of this invention does not require strict specification of any parameter such as superficial velocity of gas or liquid, pressure drop, catalyst particle size, bed void fraction or reactor dimensions. Rather, it allows for the sensible tradeoff among these conditions to satisfy an optimization criteria that may be different from one location to another, tradeoffs that would allow the use of existing equipment such as reaction vessels, compressors, or pumps, special requirements dictated by the chemistry of the catalysis to be conducted, unavailability of a certain size of catalyst, catalyst physical properties such as crush strength, and the like.

The invention has been described above with reference to numerous embodiments and specific examples. Many variations will suggest themselves to those skilled in this art in light of the above detailed description. All such obvious variations are within the full intended scope of the appended claims. Particularly preferred embodiments include: a method for determining appropriate hydraulic conditions for a process in a fixed bed reactor comprising plotting plural coordinates (Ta, φ) on a graph, each coordinate obtained by carrying out said process in a fixed bed reactor under preselected hydraulic conditions, wherein Ta is the sum of the inertia and gravity forces divided by the sum of the interface and viscous forces in said reactor for said process at a preselected point in said reactor, and φ is the volumetric gas to liquid flow ratio in said reactor for said process at said preselected point, and determining from said graph appropriate hydraulic conditions; or preferably further limited by at least one of the limitations set forth in the specification, which may be combined as would be apparent and practicable to one of ordinary skill in the art in possession of the present disclosure which may be combined as practicable, particularly: further including, after determining from said graph appropriate hydraulic conditions, carrying out said process in a fixed bed reactor under said appropriate hydraulic conditions, and/or wherein said process in said fixed bed reactor is a hydrotreating process, and/or wherein said process in said fixed bed reactor comprises a downflow, cocurrent, fixed bed hydrogenation of an organic feedstock, and/or wherein said process in said fixed bed reactor is running in a bubble flow regime, and/or wherein each coordinate (Ta, φ) is obtained under hydraulic conditions differing from the hydraulic conditions for all other coordinates (Ta, φ) on said graph by at least one of: reactor diameter, reactor length, pressure, liquid rate, gas rate, gas/liquid stoichiometry, catalyst particle size, catalyst particle shape, catalyst loading density, catalyst bed void fraction, presence or absence of recycle, recycle stoichiometry, number of vessels, and heat removal method, or wherein for each coordinate (Ta, φ), Ta is further defined by the expression $Ta=(1+1/Fr)/(We+1/Re)$, and φ is further defined by the expression $\phi=u_G/u_L$, wherein $u_G$ and $u_L$ are the superficial flow velocity of gas and liquid phases in m/s, respectively, and further wherein:

$$Fr=[(L+G)v_{LG}]^2/gD_h$$

$$We=D_h(L+G)^2 v_{LG}/\sigma_L$$

$$Re=D_h(L+G)/\mu_{LG}$$

$$v_{LG}=(L/G)v_L/(1+L/G)+v_G/(1+L/G)$$

$$\mu_{LG}=(L/G)\mu_L/(1+L/G)+\mu_G/(1+L/G)$$

$$D_h=2\epsilon D/[2+3(1-\epsilon)(D/D_p)]$$

where
D=column diameter, m
$D_h$=bed hydraulic diameter, m
$D_p$=equivalent particle diameter of catalyst, m
Fr=Froude number, unitless
G=superficial mass velocity of gas, kg/m²s
g=acceleration due to gravity, m/s²

L=superficial mass velocity of liquid, kg/m²s
Re=Reynolds number, unitless
$u_G$=ideal superficial velocity of gas at reactor temperature and pressure, m/s
$u_L$=superficial velocity of liquid, m/s
We=Weber number, unitless
$\epsilon$=void fraction of catalyst bed, unitless
$\mu_G$=viscosity of gas, kg/m·s
$\mu_L$=viscosity of liquid, kg/m·s
$\mu_{LG}$=effective viscosity of the gas-liquid mixture, kg/m·s
$\rho_G$=ideal gas density at reactor temperature and pressure, kg/m³
$\rho_L$=liquid density, kg/m³
$\sigma_L$=liquid surface tension, N/m
$\upsilon_G$=ideal specific volume of gas at reactor temperature and pressure, m³/kg,
$\upsilon_L$=specific volume of liquid, m³/kg
$\upsilon_{LG}$=specific volume of the gas-liquid mixture, m³/kg and/or wherein said process further comprises passing a feed solution comprising an organic feedstock downwardly in cocurrent with a hydrogen-containing gas through a hydrogenation zone comprising a bed of a hydrogenation catalyst, and wherein said organic feedstock comprises at least one aldehyde or ketone selected from C3-C13 aldehydes and ketones. Another particularly preferred embodiment inlcudes: a process in a fixed bed catalytic reactor operating under the following conditions:

Ta<N; and (a)

$\phi > a + (b \cdot Ta)$;

wherein variables N, a, and b are predetermined from a graph of plural (Ta, φ) coordinates according to a method for determining appropriate hydraulic conditions for a process in a fixed bed reactor comprising plotting plural coordinates (Ta, φ) on a graph, each coordinate obtained by carrying out said process in a fixed bed reactor under preselected hydraulic conditions, wherein Ta is the sum of the inertia and gravity forces divided by the sum of the interface and viscous forces in said reactor for said process at a preselected point in said reactor, and φ is the volumetric gas to liquid ratio in said reactor for said process at said preselected point, and determining from said graph appropriate hydraulic conditions, which may also be further limited by the limitation that N, a, and b are predetermined by drawing a line separating the coordinates (Ta, φ) providing acceptable results from those coordinates (Ta, φ) providing unacceptable results, said line having a y-intercept defined by the parameter "a" and a slope defined by the parameter "b" in equation (b) and having a limit of acceptable results defined by the parameter "N" in said equation, and/or wherein said process comprising passing a feed solution comprising an organic feedstock downwardly in cocurrent with a hydrogen-containing gas through a hydrogenation zone comprising a bed of a hydrogenation catalyst, under hydraulic conditions that satisfy the following equations:

10<Ta<500; and (a)

$\{0.045 + (0.00035 \times Ta)\} < \phi < 0.8$. (b)

Yet another preferred embodiment includes: a process comprising passing a feed solution comprising an organic feedstock downwardly in cocurrent with a hydrogen-containing gas through a hydrogenation zone comprising a bed of a hydrogenation catalyst, monitoring said process and taking measurements so as to calculate whether or not the following equations hold in at least one point in the reactor:

Ta<500; and (a)

$\phi > a + (b \cdot Ta)$; (b)

wherein variables a and b are predetermined, and wherein p is the gas to liquid volumetric flow ratio, and Ta is the Talmor number defined by the following equation:

$Ta = (1 + 1/Fr)/(We + 1/Re)$; (c)

wherein Fr is the Froude number, We is the Weber number, and Re is the Reynolds number, even more preferably but optionally further including calculating whether or not said equations hold for said reaction, and even more preferably but optionally wherein if said equations do not hold for said reaction, changing at least one reactor variable selected from reactor diameter, reactor length, pressure, liquid rate, gas rate, gas/liquid stoichiometry, catalyst particle size, catalyst particle shape, catalyst loading density, catalyst bed void fraction, presence or absence of recycle, recycle stoichiometry, number of vessels, and heat removal method, and yet still more preferably but optionally further including, after said changing of at least one reactor variable, repeating the steps of taking said measurements and calculating whether or not said equations hold for said reaction. Yet still other preferred embodiments include an hydrogenation process in a downilowing fixed bed reactor comprising hydraulic conditions defined by the following equations:

10<Ta<500; and (a)

$\{0.045 + (0.00035 \times Ta)\} < \phi < 0.8$; (b)

wherein p is the volumetric gas to liquid flow ratio and Ta is defined by the following equation:

$Ta = (1 + 1/Fr)/(We + 1/Re)$; (c)

wherein Fr is the Froude number, We is the Weber number, and Re is the Reynolds number; a method of producing an alcohol comprising feeding a liquid comprising an organic species comprising at least 3 carbon atoms and a reactive carbonyl moiety into a fixed bed reactor under conditions sufficient to cause hydrogenation of said reactive carbonyl moiety, said conditions including hydraulic conditions determined according to claim 1; a process for carrying out a chemical reaction in a fixed bed reactor, the process comprising providing at least one zone having a solid catalyst, a liquid phase, and a gaseous phase, under conditions sufficient to carry out a chemical reaction, the improvement comprising operating said zone under hydraulic conditions obtainable according to the method of determining appropriate hydraulic conditions for a process in a fixed bed reactor comprising plotting plural coordinates (Ta, φ) on a graph, each coordinate obtained by carrying out said process in a fixed bed reactor under preselected hydraulic conditions, wherein Ta is the sum of the inertia and gravity forces divided by the sum of the interface and viscous forces in said reactor for said process at a preselected point in said reactor, and φ is the volumetric gas to liciuid ratio in said reactor for said process at said preselected point, and determining from said graph appropriate hydraulic conditions (and a more preferred embodiment wherein said hydraulic conditions are obtained by obtaining new (Ta, φ) coordinates and comparing said new coordinates to the boundary conditions obtained from said plot of (Ta, φ) coordinates, wherein said new coordinates are obtained by changing at least one of hydraulic diameter, reactor diameter, reactor length, pressure, liquid rate, gas rate, gas/liquid stoichiometery, catalyst particle size, catalyst particle shape, catalyst loading density, number of vessels, and heat removal method, or yet still more preferably wherein said process is repeated until (Ta, φ) coordinates are obtained wherein no free $H_2$ is observed at the end of the reactor, and even still more preferably wherein heat removal methods are selected from adiabatic heat removal, heat removal by recycle with external cooling wherein the cooled recycle is injected in one or more points of the reactor, or by coils or tubes within the catalyst bed; and also a process for carrying out a chemical reaction in a fixed bed reactor comprising determining the operating conditions required for said chemical reaction, carrying out said chemical reaction in said fixed bed reactor, and obtaining at least one product from said chemical reaction, the improvement comprising: plotting plural (Ta, φ) coordinates on a graph, each coordinate obtained by carrying out said chemical reaction in said fixed bed reactor, wherein Ta is the inertia and gravity forces divided by the interface and viscous forces at a preselected point in said reactor and φ is the volumetric gas to liquid ratio at said preselected point, and obtaining from said graph boundary conditions required for said operating conditions required for said chemical reaction, and operating said chemical reaction within said boundary conditions; and also a fixed bed catalytic reactor having at least one of column diameter, column length, bed hydraulic diameter, equivalent particle diameter of catalyst, catalyst shape, and void fraction of catalyst bed determined by a process according to the above-recited processes; and also a graph comprising a plot prepared by the above-recited processes; and also the use of said graph, such as for determining appropriate reactor conditions, to produce a product, to design a reactor, to diagnose a reactor, or design a reactor part.

Trade names used herein are indicated by a ™ symbol or ® symbol, indicating that the names may be protected by certain trademark rights, e.g., they may be registered trademarks in various jurisdictions.

All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated. While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

We claim:

1. A method for determining appropriate hydraulic conditions for a process in a fixed bed reactor comprising plotting plural coordinates (Ta, φ) on a graph, each coordinate obtained by carrying out said process in a fixed bed reactor under preselected hydraulic conditions, wherein Ta is the sum of the inertia and gravity forces divided by the sum of the interface and viscous forces in said reactor for said process at a preselected point in said reactor, and φ is the volumetric gas to liquid ratio in said reactor for said process at said preselected point, and determining from said graph appropriate hydraulic conditions, said process further including, after determining from said graph appropriate hydraulic conditions, carrying out said process in a fixed bed reactor under said appropriate hydraulic conditions, with the proviso that the appropriate hydraulic conditions are characterized by Ta<600 and φ<a+(b·Ta); wherein a, and b are predetermined for a given reaction from the plot of plural (Ta, φ) coordinates.

2. The method according to claim 1, wherein for each coordinate (Ta, φ), Ta is further defined by the expression Ta=(1+1/Fr)/(We+1/Re), and φ is further defined by the expression φ=$u_G/u_L$, wherein $u_G$ and $u_L$ are the superficial flow velocity of gas and liquid phases in m/s, respectively, and further wherein:

$$Fr=[(L+G)\upsilon_{LG}]^2/gD_h$$

$$We=D_h(L+G)^2\upsilon_{LG}/\sigma_L$$

$$Re=D_h(L+G)/\mu_{LG}$$

$$\upsilon_{LG}=(L/G)\upsilon_L/(1+L/G)+\upsilon_G/(1+L/G)$$

$$\mu_{LG}=(L/G)\mu_L/(1+L/G)+\mu_G/(1+L/G)$$

$$D_h=2\epsilon D/[2+3(1-\epsilon)(D/D_p)]$$

where
D=column diameter, m
$D_h$=bed hydraulic diameter, m
$D_p$=equivalent particle diameter of catalyst, m
Fr=Froude number, unitless
G=superficial mass velocity of gas, kg/m$^2$s
g=acceleration due to gravity, m/s$^2$
L=superficial mass velocity of liquid, kg/m$^2$s
Re=Reynolds number, unitless
$u_G$=ideal superficial velocity of gas at reactor temperature and pressure, m/s
$u_L$=superficial velocity of liquid, m/s
We=Weber number, unitless
$\epsilon$=void fraction of catalyst bed, unitless
$\mu_G$=viscosity of gas, kg/m-s
$\mu_L$=viscosity of liquid, kg/m-s
$\mu_{LG}$=effective viscosity of the gas-liquid mixture, kg/m-s
$\rho_G$=ideal gas density at reactor temperature and pressure, kg/m$^3$
$\rho_L$=liquid density, kg/m$^3$
$\sigma_L$=liquid surface tension, N/m
$\upsilon_G$=ideal specific volume of gas at reactor temperature and pressure, m$^3$/kg,
$\upsilon_L$=specific volume of liquid, m$^3$/kg
$\upsilon_{LG}$=specific volume of the gas-liquid mixture, m$^3$/kg.

3. The method according to claim 1, wherein said process in said fixed bed reactor is a hydrotreating process.

4. The method according to claim 1, wherein said process in said fixed bed reactor comprises a downflow, cocurrent, fixed bed hydrogenation of an organic feedstock.

5. The method according to claim 1, wherein said process in said fixed bed reactor is running in a bubble flow regime.

6. The method according to claim 1, wherein each coordinate (Ta, φ) is obtained under hydraulic conditions differing from the hydraulic conditions for all other coordinates (Ta, φ) on said graph by at least one of: reactor diameter, reactor length, pressure, liquid rate, gas rate, gas/liquid stoichiometry, catalyst particle size, catalyst particle shape, catalyst loading density, catalyst bed void fraction, presence or absence of recycle, recycle stoichiometry, number of vessels, and heat removal method.

7. The process according to claim 1, wherein said process further comprises passing a feed solution comprising an organic feedstock downwardly in co-current with a hydrogen-containing gas through a hydrogenation zone comprising a bed of a hydrogenation catalyst, and wherein said organic feedstock comprises at least one aldehyde or ketone selected from C3-C13 aldehydes and ketones.

8. A method of producing an alcohol comprising feeding a liquid comprising an organic species comprising at least 3 carbon atoms and a reactive carbonyl moiety into a fixed bed reactor under conditions sufficient to cause hydrogenation of said reactive carbonyl moiety, said conditions including hydraulic conditions determined according to claim 1.

9. In a process for carrying out a chemical reaction in a fixed bed reactor, the process comprising providing at least one zone having a solid catalyst, a liquid phase, and a gaseous phase, under conditions sufficient to carry out a chemical reaction, the improvement comprising operating said zone under hydraulic conditions obtainable according to the method of claim 1.

* * * * *